United States Patent
Chang et al.

(10) Patent No.: US 10,251,770 B2
(45) Date of Patent: Apr. 9, 2019

(54) LUBRICATED VALVE FOR OSTOMY POUCH

(71) Applicant: Hollister Incorporated, Libertyville, IL (US)

(72) Inventors: Moh-Ching Oliver Chang, Lake in the Hills, IL (US); Jon Z. Lugenbill, Warrenville, IL (US); Kevin Harrington, Libertyville, IL (US); Daniel March, Lake Villa, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 978 days.

(21) Appl. No.: 14/563,542

(22) Filed: Dec. 8, 2014

(65) Prior Publication Data

US 2015/0190272 A1 Jul. 9, 2015

Related U.S. Application Data

(60) Provisional application No. 61/923,497, filed on Jan. 3, 2014.

(51) Int. Cl.
 *A61F 5/44* (2006.01)
 *A61F 5/445* (2006.01)
 *A61L 28/00* (2006.01)

(52) U.S. Cl.
 CPC ............ *A61F 5/4405* (2013.01); *A61F 5/445* (2013.01)

(58) Field of Classification Search
 CPC combination set(s) only.
 See application file for complete search history.

(56) References Cited

U.S. PATENT DOCUMENTS

| 4,123,409 A | * | 10/1978 | Kaelble | A61L 15/58 523/118 |
|---|---|---|---|---|
| 4,218,510 A | | 8/1980 | Wilson | |
| 4,280,498 A | | 7/1981 | Jensen | |
| 4,419,410 A | | 12/1983 | Weiner | |
| 4,524,099 A | | 6/1985 | Di Luccio | |
| 4,590,125 A | | 5/1986 | Balloni et al. | |
| 4,810,541 A | | 3/1989 | Newman et al. | |
| 5,216,043 A | | 6/1993 | Sipinen | |
| 5,470,526 A | | 11/1995 | Wilfong et al. | |
| 5,543,477 A | * | 8/1996 | Latiolais | C08F 8/44 525/227 |
| 5,552,096 A | * | 9/1996 | Auda | C08F 8/00 159/2.1 |
| 5,565,161 A | * | 10/1996 | Auda | C08F 8/00 159/2.1 |
| 5,639,810 A | * | 6/1997 | Smith, III | A61L 29/041 524/269 |

(Continued)

FOREIGN PATENT DOCUMENTS

| EP | 2620168 A1 | 7/2013 |
|---|---|---|
| GB | 2125130 A | 2/1984 |
| JP | 2013543788 A | 12/2013 |

OTHER PUBLICATIONS

European Search Report for EP 14198160 dated May 4, 2015.

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

A valve for a pouch for collecting biological fluids includes a valve stem, at least a portion of which is formed from a polymeric material including oleamide.

7 Claims, 12 Drawing Sheets

(56) References Cited

U.S. PATENT DOCUMENTS

| | | | |
|---|---|---|---|
| 5,674,820 A * | 10/1997 | Manka | C10M 141/10 508/287 |
| 5,732,745 A | 3/1998 | Lefebvre et al. | |
| 5,804,675 A * | 9/1998 | Latiolais | C08F 8/44 526/329 |
| 6,103,674 A * | 8/2000 | Nalesnik | C07F 11/005 508/334 |
| 6,191,233 B1 * | 2/2001 | Kishine | C07D 251/32 522/167 |
| 6,194,361 B1 * | 2/2001 | Gatlin | C09K 8/035 507/239 |
| 6,291,063 B1 | 9/2001 | Shah et al. | |
| 6,497,965 B1 | 12/2002 | Longmoore et al. | |
| 6,869,653 B2 | 3/2005 | Ling et al. | |
| 7,087,314 B2 | 8/2006 | Forte et al. | |
| 7,736,726 B2 | 6/2010 | McAllister, Jr. et al. | |
| 7,799,436 B2 | 9/2010 | Wieners et al. | |
| 7,902,093 B2 | 3/2011 | Dharmarajam et al. | |
| 7,998,579 B2 | 8/2011 | Lin et al. | |
| 8,202,612 B2 | 6/2012 | Brennan et al. | |
| 9,492,363 B1 * | 11/2016 | Lueschen | A61Q 1/00 |
| 9,707,162 B2 * | 7/2017 | De Szalay | A01N 31/02 |
| 2005/0031886 A1 | 2/2005 | Forte et al. | |
| 2005/0177133 A1 | 8/2005 | Nielsen et al. | |
| 2008/0274071 A1 * | 11/2008 | Kaplan | A61K 8/02 424/70.11 |
| 2009/0209922 A1 | 8/2009 | Boisjoly | |
| 2010/0047202 A1 * | 2/2010 | Goddinger | A61K 8/731 424/70.12 |
| 2010/0048437 A1 * | 2/2010 | Brown | C10M 129/72 508/283 |
| 2010/0055137 A1 * | 3/2010 | Larm | A61K 9/1075 424/401 |
| 2010/0068355 A1 | 3/2010 | Berry et al. | |
| 2010/0092793 A1 | 4/2010 | Aithani et al. | |
| 2010/0125114 A1 | 5/2010 | Williams et al. | |
| 2010/0256590 A1 | 10/2010 | Babrowicz et al. | |
| 2011/0202028 A1 | 8/2011 | Toro et al. | |
| 2011/0202029 A1 | 8/2011 | Toro et al. | |
| 2011/0253152 A1 | 10/2011 | Lin et al. | |
| 2011/0269911 A1 * | 11/2011 | Morita | C08F 214/22 525/326.2 |
| 2012/0046401 A1 | 2/2012 | Llop et al. | |
| 2012/0077924 A1 * | 3/2012 | Ota | C08K 3/04 524/495 |
| 2012/0077925 A1 * | 3/2012 | Terada | C09K 3/1009 524/495 |
| 2012/0077926 A1 * | 3/2012 | Ota | C08K 3/04 524/495 |
| 2012/0077927 A1 * | 3/2012 | Ota | C08K 5/0025 524/495 |
| 2012/0077939 A1 * | 3/2012 | Ota | C08K 3/04 525/326.3 |
| 2012/0130329 A1 | 3/2012 | March et al. | |
| 2012/0095150 A1 * | 4/2012 | Ota | C08K 5/0025 524/495 |
| 2013/0217604 A1 * | 8/2013 | Fisk, Jr. | B01F 17/0021 507/131 |
| 2014/0127141 A1 * | 5/2014 | Ijaz | A01N 31/02 424/45 |
| 2014/0140935 A1 * | 5/2014 | Ijaz | A01N 59/20 424/45 |
| 2014/0212361 A1 * | 7/2014 | Ijaz | A01N 59/20 424/45 |
| 2015/0126946 A1 * | 5/2015 | Fernandez | A61F 5/448 604/342 |
| 2015/0190272 A1 * | 7/2015 | Chang | A61F 5/4405 604/335 |
| 2015/0250183 A1 * | 9/2015 | Apollo | A01N 31/02 424/641 |
| 2015/0327544 A1 * | 11/2015 | Apollo | A01N 31/02 424/43 |
| 2016/0158122 A1 | 6/2016 | De Szalay | A01N 31/02 424/638 |
| 2018/0110714 A1 * | 4/2018 | Glenn, Jr. | A45D 34/00 |

\* cited by examiner

LUBRICATED VALVE FOR OSTOMY POUCH

BACKGROUND

The present disclosure is directed to a valve for an ostomy pouch. More particularly, the present disclosure pertains to a valve, for draining liquid waste or bodily fluids, for example, from a urostomy pouch.

A urostomy appliance or pouch is a medical device that provides a means for the collection of liquid waste formed via an opening into the urinary system that is diverted externally of the body through a stoma.

The waste collected in the pouch may be retained in the pouch, for example, during the daytime, so that the user can discharge or empty the pouch at a convenient time and location. The waste can also be routed out of the pouch, for example, during the evening, directly to a remote collection container (e.g., to a leg bag, a night drainage collector, or a bedside drainage collector.)

To provide the retention or routing function, a valve is disposed at the bottom or discharge end of the pouch. A typical valve is a plastic ball-cock or pet-cock type valve that includes a fixed body and a rotating cylindrical valve stem. An opening in the valve body provides fluid communication from the pouch into a circumferentially disposed section of the body on a side of the stem. The stem includes an opening that extends circumferentially about a portion of the stem that is open to a central opening in the stem. In this manner the stem is rotated 180 degrees between an open position, in which the body opening and stem opening are aligned and a closed position, in which the body opening and the stem opening are not in alignment. For example, US patent application publication number US 2012/0130329, which is commonly assigned with the present application and incorporated herein by reference, discloses such a valve for ostomy applications.

Users of a urostomy pouches may be ill and weak, especially shortly after undergoing urostomy surgery. As such, it is crucial to provide a valve that can be rotated easily between the open and closed positions. One known method of facilitating valve rotation is application of a lubricant, such as silicone oil, directly onto a valve stem and/or valve body to reduce friction therebetween.

Although, such topical application of silicone oil can provide a sufficiently low torque initially, after an extended period of time in storage, silicone oil has a tendency for flowing away from where it is needed and leaving "dry spots" in some contact areas between the valve stem and valve body. This can significantly increase the torque required to rotate the valve and cause undesirable valve sticking. For example, the torque of a valve topically lubricated with silicone oil can increase from about 1 in·lbs to greater than about 3 in·lbs after one month shelf time.

Accordingly, there is a need for an improved valve for a urostomy pouch that can provide a sufficiently low initial torque, which can be maintained after an extended storage and throughout the life of the valve.

BRIEF SUMMARY

It is crucial that a valve for a pouch for collecting biological fluids, such as a urostomy pouch, can be easily manipulated by users. To provide a valve having a sufficiently low torque for easy opening and closing of the valve, the valve may be lubricated with oleamide. For example, a valve may be made using a polymeric compound comprising oleamide. Such a valve comprising oleamide can maintain a low torque even after an extended period of time in storage and throughout the life of a valve In one aspect, a valve that is sealable to an associated container and adapted to permit and stop flow of fluid from the container is provided. The valve may include a valve body, which is sealable to the container, and a valve stem. The valve body may have a stem receiving region formed therein and may include a fluid receiving region in communication with the container interior. The valve stem may be mounted to the valve body and may include a hollow tubular member defining a central bore. The valve stem may be positioned in the stem receiving region and may be adapted for rotation within the stem receiving region. The valve stem also may include a stem opening in a portion of a wall thereof. The valve stem may be rotatable between an open position to align the stem opening with the valve body fluid receiving region to permit flow from the fluid storage region through the valve, and a closed position to misalign the stem opening with the valve body fluid receiving region to stop flow through the valve. The valve stem may also include a grasping portion spaced from the valve body, which is adapted to rotate the valve stem within the stem receiving region to move the valve between the open and closed positions. Further, at least a portion of the valve stem that is in contact with the stem receiving region may be formed from a material comprising at least about 0.1 wt. % oleamide.

Preferably, at least the portion of the valve stem that is in contact with the stem receiving region is formed from a material comprising about 0.5 wt. % to about 5 wt. % oleamide, and more preferably, a material comprising about 1.5 wt. % to about 2 wt. % oleamide.

In one embodiment, at least the portion of the valve stem that is in contact with the stem receiving region may be formed from a material comprising oleamide and a polyethylene based polymer or a polypropylene based polymer. For example, the valve stem may be formed from a material comprising about 98 wt. % to about 98.5 wt. % of a polyethylene blend including high density polyethylene, linear low density polyethylene, low density polyethylene (HDPE/LLDPE/LDPE) and about 1.5 wt. % to about 2 wt. % oleamide.

Further, the grasping portion of the valve stem may include a frame. In some embodiments, the hollow tubular member and the frame may be formed as a unitary member, which can be formed from a material comprising about 98 wt. % to about 98.5 wt. % HDPE/LLDPE/LDPE and about 1.5 wt. % to about 2 wt. % oleamide. Further, at least a portion of the valve body that is in contact with the valve stem may be formed from a polymeric material comprising about 0.01 wt. % to about 0.5 wt. % oleamide.

In any of the above discussed valve embodiments, the valve may be configured to have an average torque value of about 0.5 in·lbs to about 2.0 in-lbs, which can be maintained even after one month in storage and throughout 5 days of using the valve.

In another aspect, a medical device for collecting biological fluids is provided. The medical device may include a pouch defining a collection chamber therein, an inlet opening for receiving biological fluids, an outlet opening defined in a bottom portion of the pouch, and a valve adapted to permit and stop flow of biological fluids collected in the collection chamber. The valve may include a valve body, which may be sealed to the pouch in the bottom portion proximate the outlet opening, and a valve stem mounted to the valve body. The valve body may include a stem receiving region formed therein, and a fluid receiving region in communication with the collection chamber. The valve stem may include a hollow tubular member defining a central bore. The valve stem may be positioned in the stem receiving region and adapted for rotation within the stem receiving region. The valve stem may also include a stem opening in a portion of a wall thereof. The valve stem may be rotatable between an open position to align the stem opening with the valve body fluid receiving region to permit flow from the collection chamber through the valve, and a closed position to misalign the stem opening with the valve body fluid receiving region to stop flow through the valve. The valve stem may also include a grasping portion spaced from the valve body, which is adapted to facilitate rotating of the valve stem within the stem receiving region to move the valve between the open and closed positions. Further, at least a portion of the valve stem that is in contact with the stem receiving region may be formed from a material comprising at least about 0.1 wt. % oleamide.

Preferably, at least the portion of the valve stem that is in contact with the stem receiving region is formed from a material comprising about 0.5 wt. % to about 5 wt. % oleamide, and more preferably, a material comprising about 1.5 wt. % to about 2 wt. % oleamide.

In one embodiment, at least the portion of the valve stem that is in contact with the stem receiving region may be formed from a material comprising oleamide and a polyethylene based polymer or a polypropylene based polymer. For example, the valve stem may be formed from a material comprising about 98 wt. % to about 98.5 wt. % HDPE and about 1.5 wt. % to about 2 wt. % oleamide.

Further, the grasping portion of the valve stem may include a frame. In some embodiments, the hollow tubular member and the frame may be formed as a unitary member, which can be formed from a material comprising about 98 wt. % to about 98.5 wt. % HDPE/LLDPE/LDPE and about 1.5 wt. % to about 2 wt. % oleamide. Further, at least a portion of the valve body that is in contact with the valve stem may be formed from a polymeric material comprising about 0.01 wt. % to about 0.5 wt. % oleamide.

In any of the above discussed medical device embodiments, the valve may be configured to have an average torque value of about 0.5 in·lbs to about 2.0 in-lbs, which can be maintained even after one month in storage and throughout 5 days of using the valve.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein:

FIG. 1A is a sectional view taken along line 1A-1A of FIG. 1;

DETAILED DESCRIPTION

Figure 1:
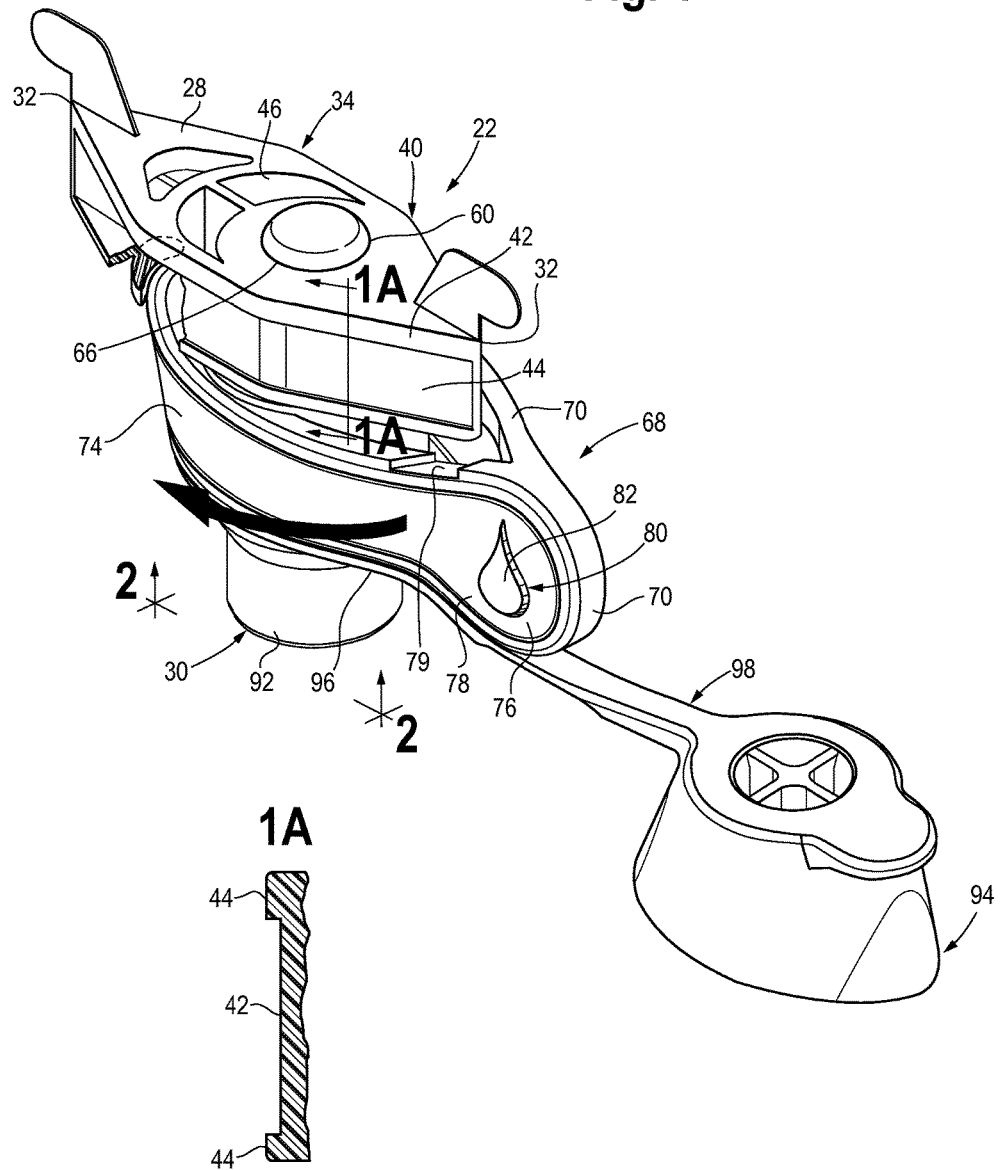
FIG. 1 is a perspective view of a valve for an ostomy pouch according to an embodiment.

While the present disclosure is susceptible of embodiment in various forms, there is shown in the drawings and will hereinafter be described a presently preferred embodiment with the understanding that the present disclosure is to be considered an exemplification and is not intended to limit the disclosure to any specific embodiment illustrated.

Figure 3:
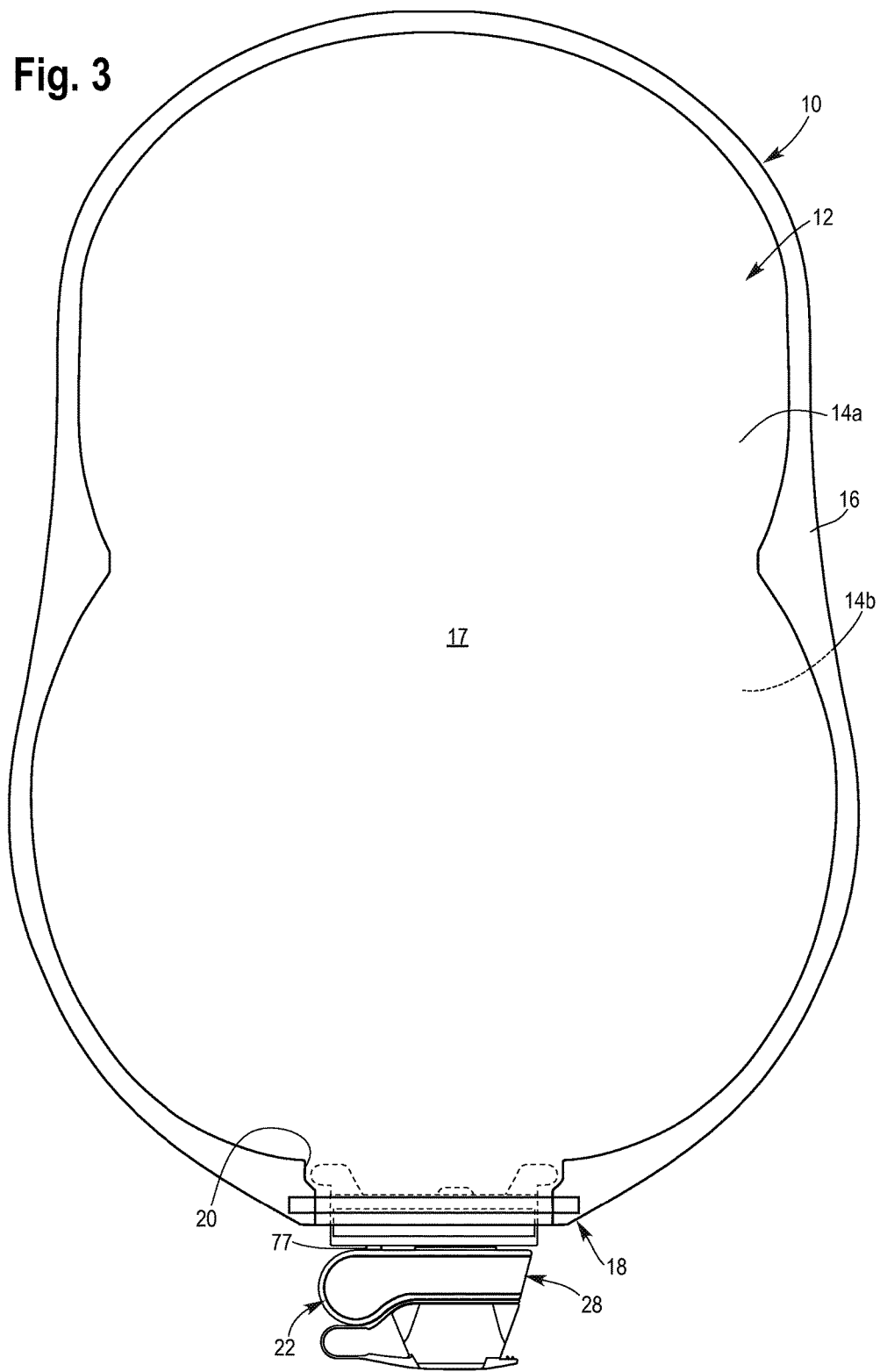
FIG. 3 is a front view of an exemplary pouch having the ostomy valve mounted thereto.

Referring now to the figures and briefly first to FIG. 3, there is shown an embodiment of an urostomy pouch 10 having a body 12 formed by, for example, sealing two films 14a,b to one another about their respective peripheries 16 to define an interior storage region 17. The bottom 18 of the pouch 10 includes an opening 20 into which a valve 22 is fitted and secured. The films 14a,b may be sealed to one another by methods such as heat sealing and the like; the valve 22 may be similarly sealed to the pouch 10 at the bottom opening 20. Suitable methods for sealing the pouch walls/films 14 to one another and valve 22 to the pouch films 14 will be recognized by those skilled in the art.

For purposes of the present disclosure and discussion, reference to "bottom," is intended to refer to the lower portion of the pouch 10 and/or valve 22 when the pouch 10 is adhered to a user's body.

Figure 4:
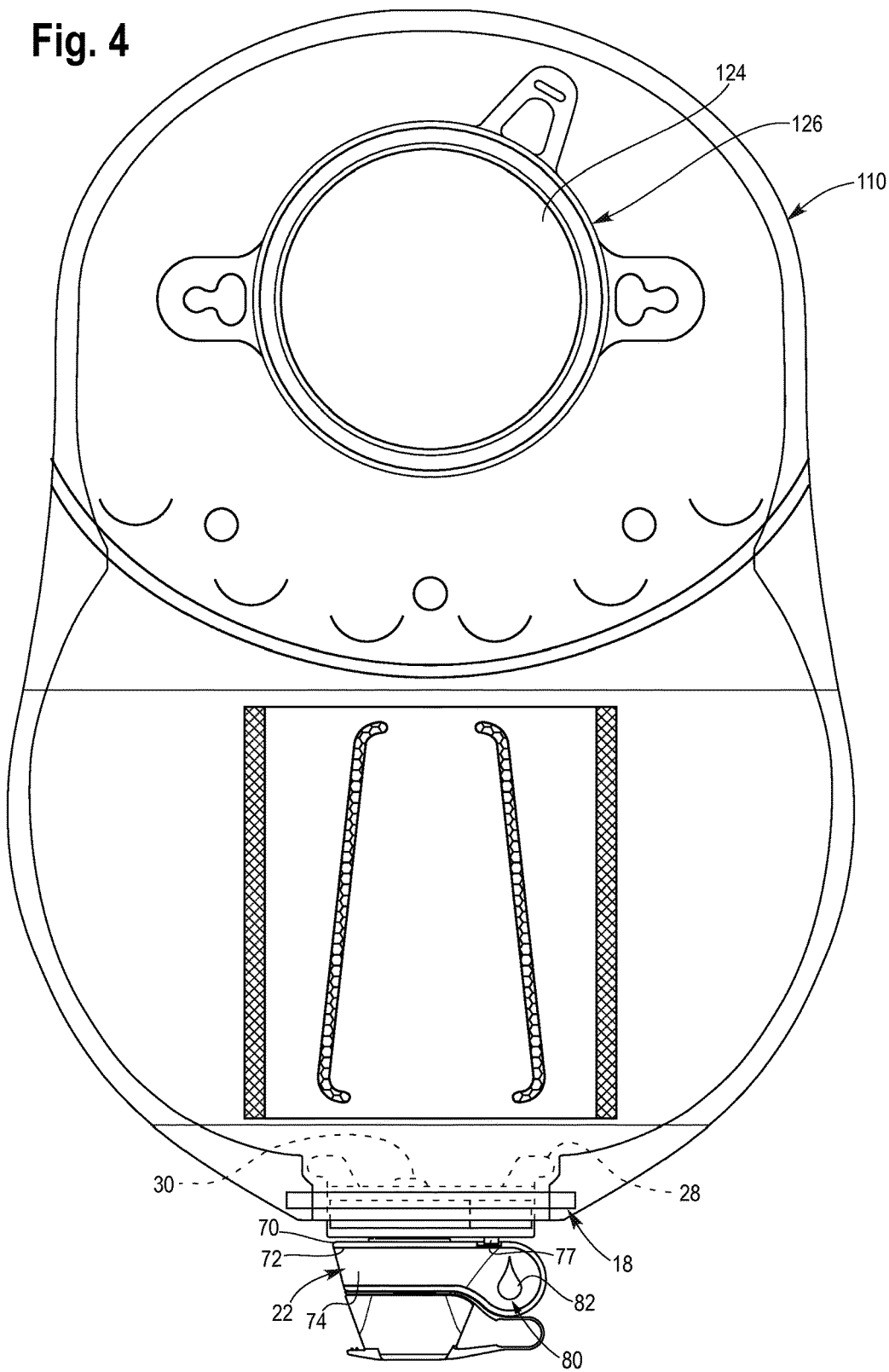
FIG. 4 is a rear view of another exemplary pouch having the ostomy valve mounted thereto.
Figure 5:
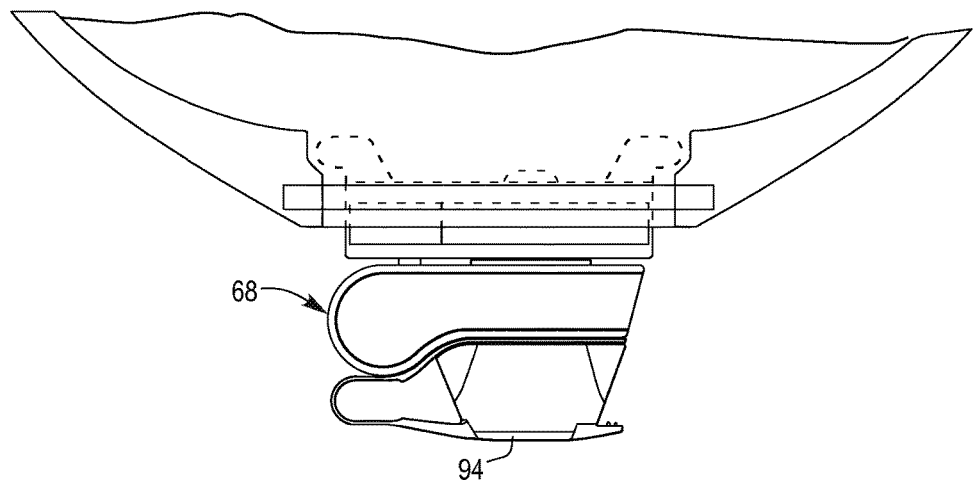
FIG. 5 is an enlarged rear view of the pouch and valve illustrated in FIG. 3.
Figure 6:
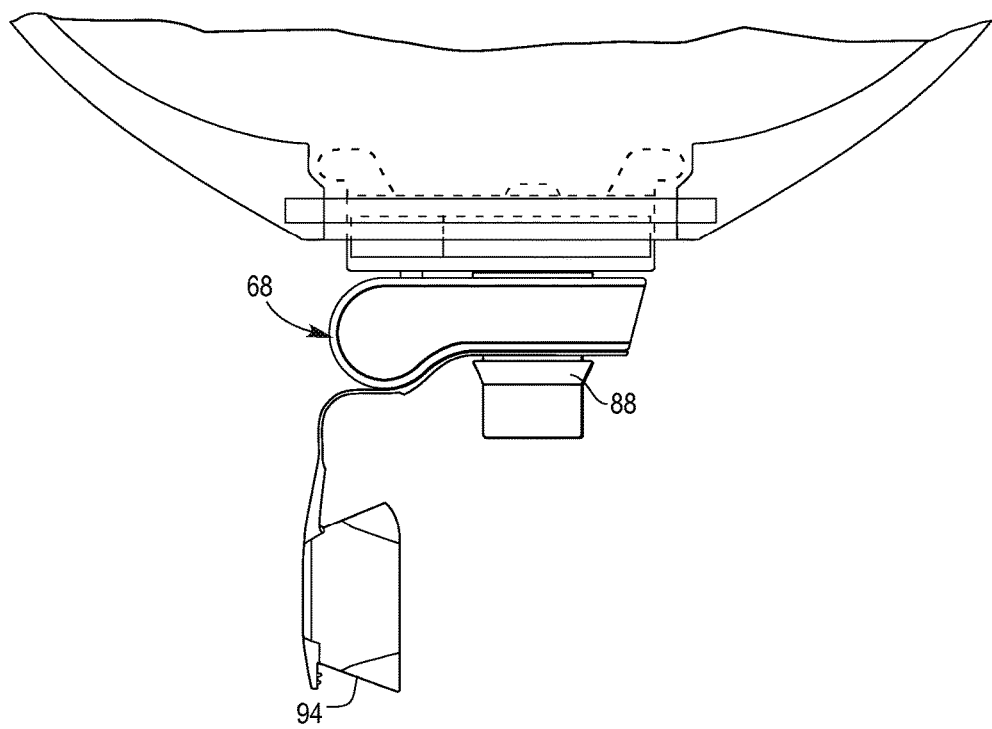
FIG. 6 is a view of the pouch and valve of FIG. 5 shown with the cap removed.

As seen in FIG. 4, which shows an alternate pouch 110, the pouch 110 includes an input opening 124 through which waste is input to the pouch 110 from a stoma. The input opening 124 may be adhered to the user by a barrier (not shown) in a one-piece or two-piece configuration (the two-piece configuration being shown generally at 126, in FIG. 4), which configurations will also be recognized by those skilled in the art.

The valve 22 may be attached and sealed to the pouch bottom 18. Accordingly, the valve 22 may include a body 28 that is sealed to the pouch films 14a,b and a stem portion 30 that is supported in and by the body 28. The stem portion 30 may be movable, e.g., rotatable, to open and close the valve 22 (e.g., to permit and isolate flow from the pouch 10).

Figure 10:
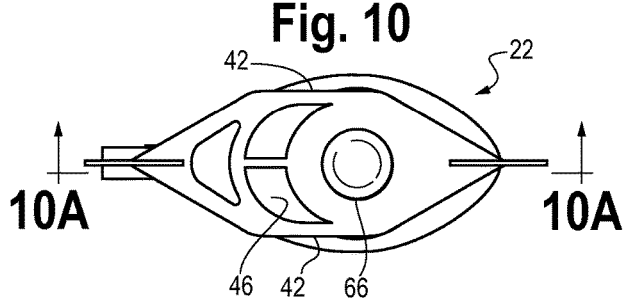
FIG. 10 is a top view of the valve.
Figure 10A:
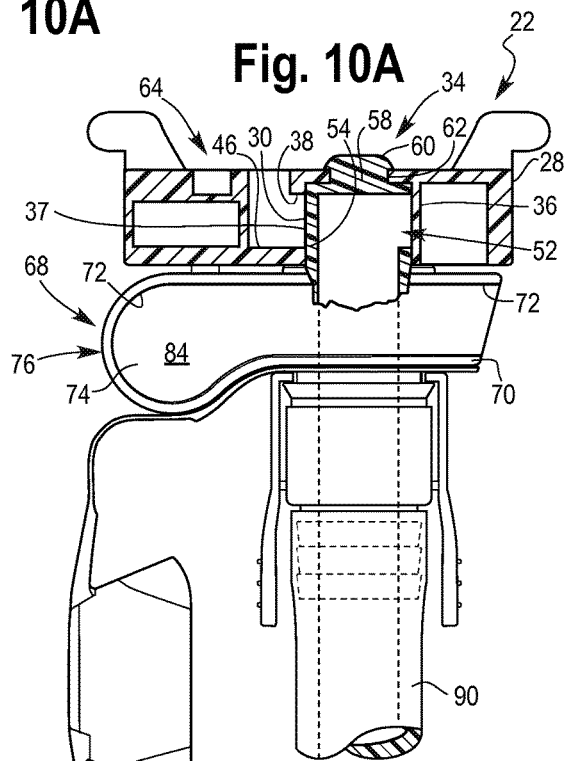
FIG. 10A is a cross-sectional illustration taken along line 10A-10A of FIG. 10, the valve shown in the closed position.
Figure 10B:
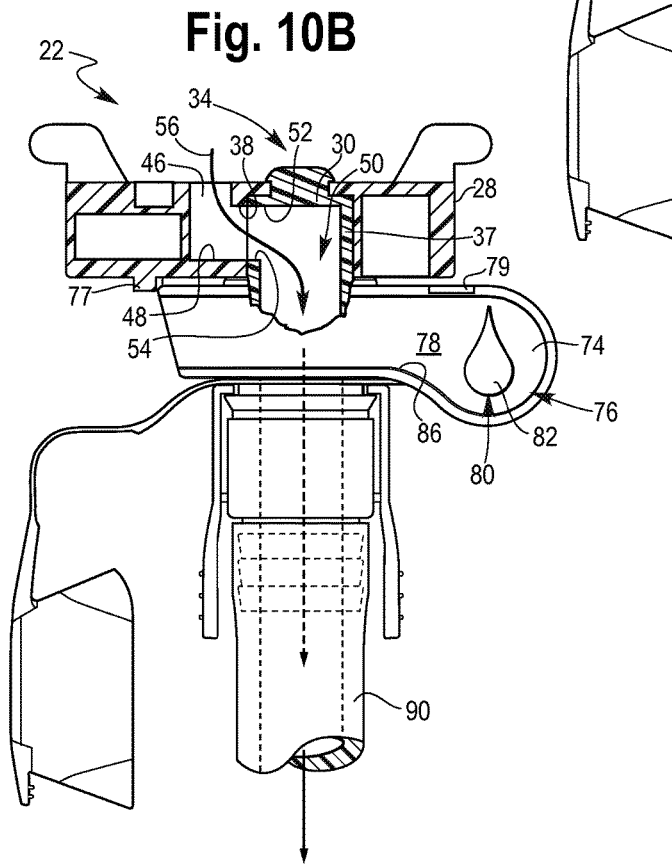
FIG. 10B is a cross-sectional illustration similar to FIG. 10A with the valve shown in the open position.

The valve body 28, as seen in FIG. 1, may have a generally elongated honeycomb shape having diverging/ converging ends 32 and an elongated central portion 34. Referring to FIGS. 10-10B, a cylindrical wall 36 may define a stem receiver or receiving region, which wall 36 may be partially open as indicated at 38, and as described below. The wall 36 may extend through the central portion 34 of the body 28. The illustrated body 28 has angular intersections, indicated generally at 40 in FIG. 1, of the various sides (e.g., central portion 34 with diverging/converging ends 32); however, it will be appreciated by those skilled in the art that the intersections may be rounded as well, and that such configurations are within the scope and spirit of the present disclosure.

The sides of the valve 22, as indicated at 42, may be formed having multiple sealing surfaces or ribs 44, as seen in FIG. 1, or may define contiguous planar sealing surfaces. The sealing surfaces 44 (whether contiguous or multiple) may be configured to provide a region at which the pouch walls 14a,b are sealed to the valve body 28 to effect a seal of the pouch 10 at the lower or bottom end 18.

The valve body 28 may include a well 46, between the side walls 42 and further defined by a bottom wall 48 and the partially open cylindrical wall or stem receiver 36. In a present valve 22, the cylindrical wall 36 serves as a seat such that fluid may pass through the valve body 28 and into the stem portion 30; that is, fluid can pass from the well 46 through the opening 38.

The stem portion 30 may be positioned for rotation in the stem receiver 36. The stem portion 30 may include a hollow tubular member 37 that includes a central bore 50 and an opening 52 in a part of the side wall 54 that, when the valve 22 is in the open position, is aligned with the stem receiver opening 38. In this manner a flow path is provided, as indicated at 56 in FIG. 10B, from the pouch 10, into the valve body well 46, through the aligned openings 38, 52 and out through the stem bore 50. Conversely, when the stem receiver opening 38 and stem opening 52 are not aligned (as seen in FIG. 10A), that is, when the stem portion 30 is rotated 180°, the valve is in the closed position and flow through the valve 22 is stopped. It will be appreciated that the openings 38, 52 are aligned over a portion of the rotation of the stem portion 30, and not just when the stem portion is rotated 180°. Accordingly, rotation of the stem portion 30 may be used to regulate or control flow through the valve at rotations up to and including 180°.

Figure 12:
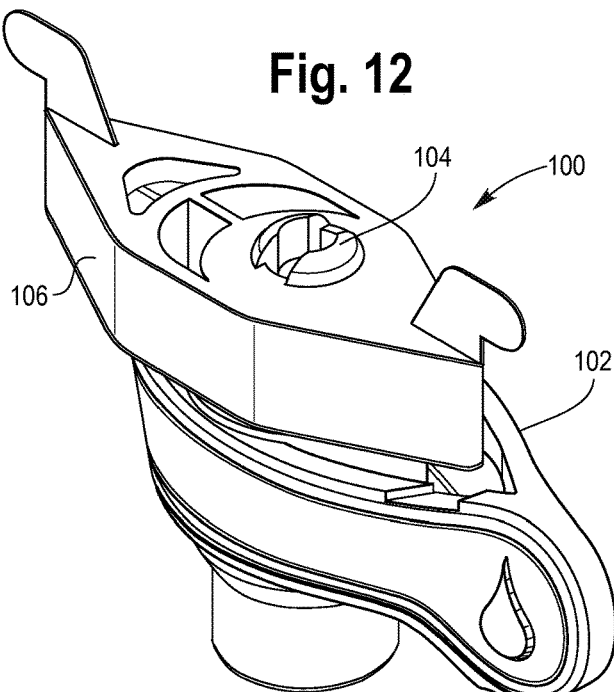
FIG. 12 is a perspective view of a valve for an ostomy pouch according to another embodiment.
Figure 13:
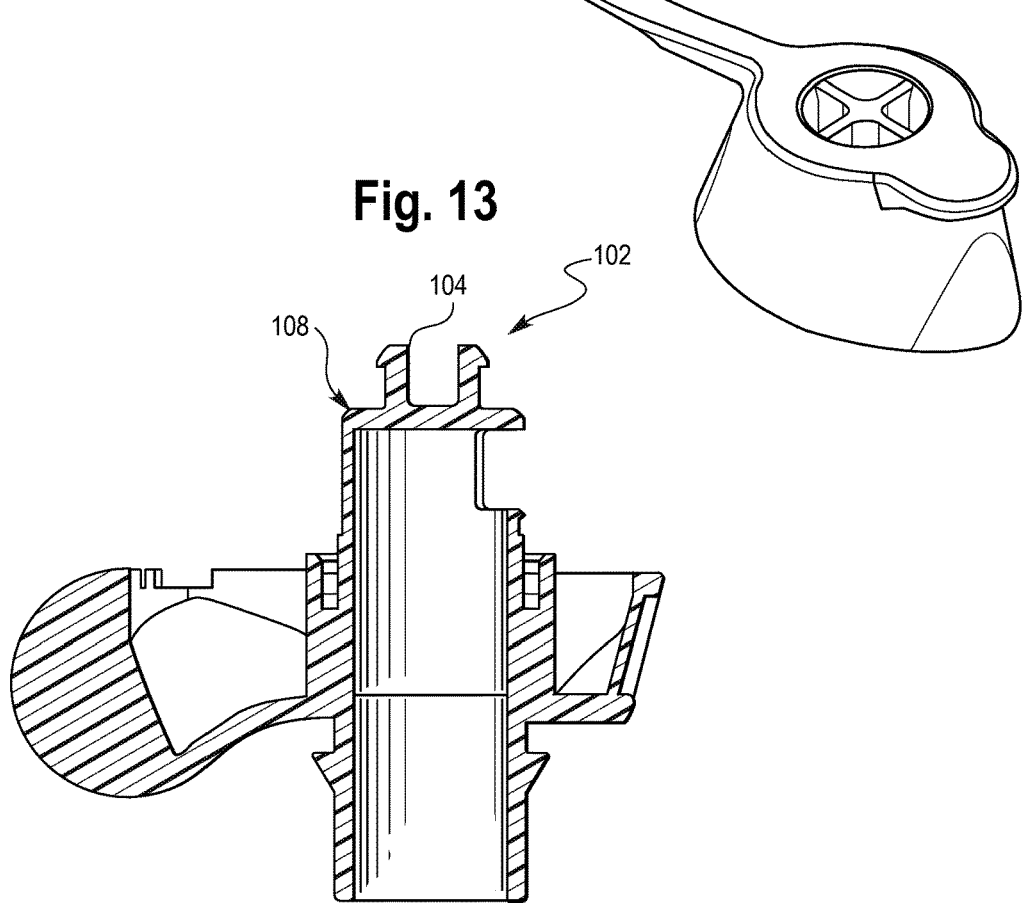
FIG. 13 is a cross sectional view of a stem portion of the valve of FIG. 12.

An upper end 58 of the stem portion 30 may include an enlarged head portion or knob 60 that fits into an opening 62 in an upper portion of the valve body 28 to secure the stem portion 30 in place in the valve body 28. The head 60 may be formed as a solid post as indicated at 66. Alternatively, the head 60 may be formed with a split configuration as shown in FIGS. 12 and 13.

The stem portion 30 may include a grasping region 68 to permit manually rotating the stem portion 30 between the open and closed positions. The grasping region 68 may be formed as a two-part member, the first part 70 being a frame or carrier that defines an outer bound 72 of the grasping region 68 and may be formed integral with the stem cylindrical wall or tubular portion 37. The second part 74 may be a tactile element that is disposed within the frame 70. The tactile element 74 may have a different "feel" from the frame portion 70. In one example, the tactile portion 74 may be formed from a material that is softer (e.g., a material having a lower durometer or surface hardness as compared to the material making up the first part 70) and has a higher frictional coefficient than the frame portion 70. It will be appreciated that this higher frictional coefficient provides a no-slip or lesser slip surface than the frame portion 70 for a more positive hold on the stem grasping region 68.

The grasping region 68 may also have an enlarged end portion 76. The enlarged end 76 provides a larger area by which a user can grasp and manually manipulate (e.g., rotate) the stem portion 30 to open and close the valve 22. The valve further includes a stop to prevent over-rotation of the valve 30. In one example, the stop may comprise a depending stub 77 on the valve body 28 and a recess 79 in the grasping portion 68. The stub 77 engages the recess 79 to stop rotation of the stem portion 30.

Figure 2:
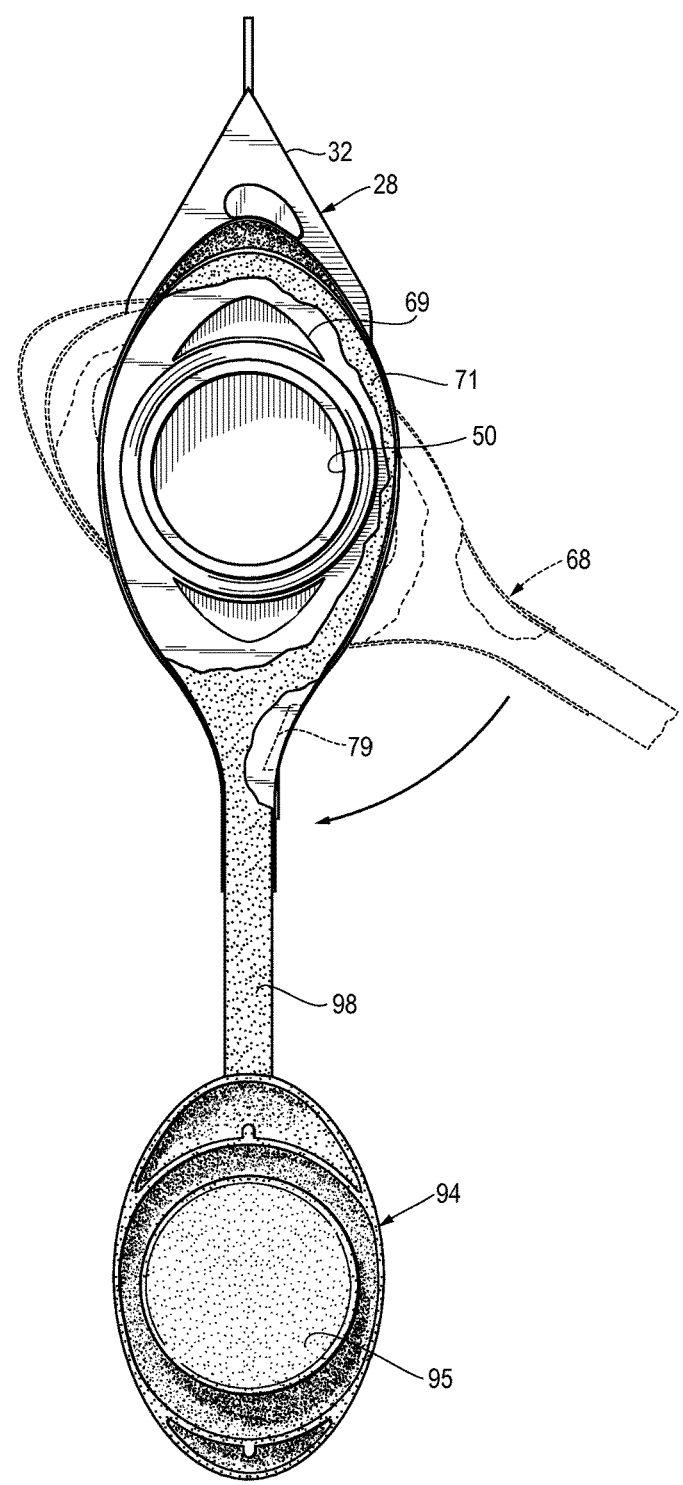
FIG. 2 is a plan view as seen along line 2-2 of FIG. 1.

One side 78 of the end 76 may include an indicator 80 that is sensed by touch (that is, also tactile), so that a user can determine from touch only, the state or position of the valve 22. In a present valve 22, the indicator 80 is a raised element 82 in the shape of a drop or tear-drop that is formed on one side 78 of the end 76; the other side 84 of the end 76 is devoid of the tactile indicator 80 (the raised drop formation 82). The drop formation 82 may be formed as part of and from the same material as the frame 70. In this manner, the drop 82 has a raised surface, raised above the tactile portion 74, and is of a different material than the surrounding tactile portion 74 or frictional surface to provide positive tactile indication of the valve 22 position. Referring briefly to FIG. 2, the grasping region 68, which may be an open molded part, may include drainage openings 69 in a bottom surface 71 to permit the drainage of fluid therefrom, for example, following a shower during which water may enter the grasping portion 68.

The stem portion 30 may be molded as a unitary member, in which the grasping portion frame 70 is formed integral with the hollow tubular portion 37. In this configuration, the grasping portion 68 is molded as part of the frame 70, with a bounding wall or edge 72 and a recessed area 86 within the bounding wall 72, and the raised drop formation 82, is also formed as part of and supported by the frame 70.

The higher friction tactile element 74 is positioned within the recessed area 86 in the grasping region 68. In a present valve 22, the higher friction tactile element 74 is molded into the recessed area 86, such as in an overmold process, between the bounding walls 72 and around the raised element 82.

The higher friction tactile element 74 may be formed from a thermoplastic elastomer (TPE) such as that available from PolyOne Corp. under the trade name DYNAFLEX®. A current material includes TPE that has a polypropylene resin added at about 10 wt. % to the material composition.

Figure 11:
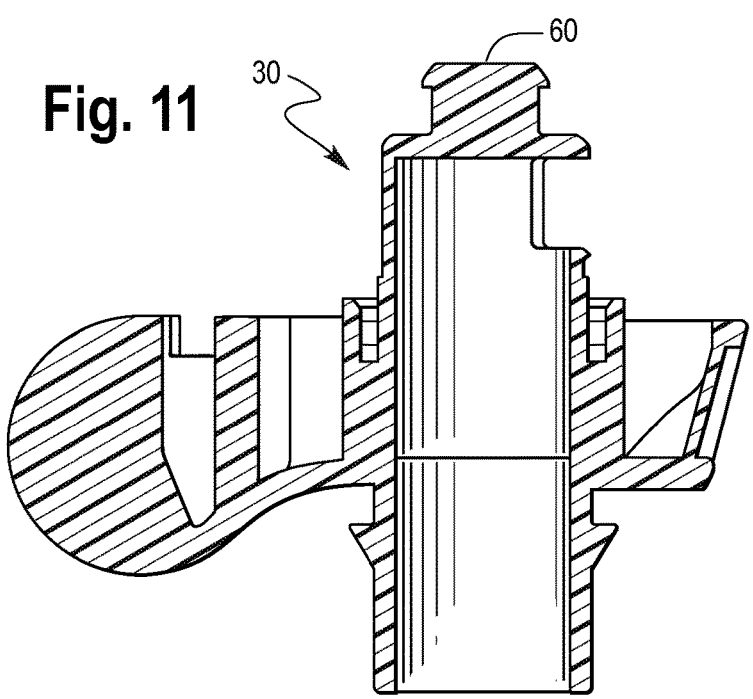
FIG. 11 is a cross sectional view of a stem portion of the valve of FIG. 1.

The stem portion 30, as best shown in FIG. 11, may be molded from a relatively rigid material that when molded and cured or hardened has a relatively smooth finish. One such material is a plastic or polymeric material such as a high density polyethylene (HDPE). It is desirable to configure a valve to provide smooth manipulation or rotation of the stem portion 30 within the body 28; that is smooth, unfettered movement of the stem portion 30 between the open and closed position. This is particularly crucial for a valve for a urostomy pouch, since users are often ill or weak and have difficulties in manipulating a valve with a high torque.

Thus, to provide for smooth manipulation of the valve, silicone oil may be applied on the stem portion 30 and/or the body 28. For example, a stem portion 30 may be lubricated with silicone oil in amount of about 0.05 g/part to about 0.1 g/part. Initially, such a topical lubricating method can provide a sufficiently low torque for a valve. However, the silicone oil has a tendency to flow down and leave "dried spots" in some contact areas as a valve sits for an extended period of time. This can increase the torque of a valve substantially, such that the valve becomes too difficult to manipulate for urostomy pouch users. For example, it was found that an initial torque of a valve lubricated with silicone oil increased from about 1 in·lbs to greater than 3 in·lbs after one month in storage. Further, this method requires an extra production step for topical application of a lubricant.

To minimize production steps and to provide a valve that can maintain a low torque after an extended time in storage, a lubricating agent may be mixed or compounded with a material for the valve stem and/or valve body. A lubricating agent, as used herein, is a material that can decrease friction between contact surfaces and reduce the torque required to rotate the valve. It is also referred to herein as a lubricant or a slip agent. For example, a stem portion 30 can be formulated including HDPE and a lubricating agent to lower the valve rotating torque. However, experiments have shown that many lubricating agents did not provide the desired low torque for smooth operation of the valve, or required such a high lubricant quantity to achieve sufficiently low torque that the lubricant migrated to the surface of the valve and abraded off or delaminated from the surface. Further, some lubricating agents provided sufficiently low initial torque, but the torque increased with the number of valve actuations during use. That is, the torque increased throughout the valve life, and the valve became stiffer and more difficult to manipulate toward the end of the valve life.

After extensive research, it was discovered that a valve formulated with oleamide can provide a sufficiently low initial torque, which can be maintained even after an extended time in storage and throughout the valve life. For example, a valve stem 30 and/or valve body 28 may be formulated with HDPE and at least about 0.1 wt. % of oleamide, preferably at least about 0.5 wt. %, and more preferably about 1 wt. % to about 5 wt. % oleamide. In one preferred embodiment a valve stem 30 may be formulated with HDPE and about 1.5 wt. % to about 2 wt. % oleamide. This was a surprising finding since field evaluations of valves comprising other similar slip agents, such as erucamide, indicated that torque of such valves increased incrementally throughout valve life and became undesirably stiff for urostomy pouch users. Other suitable polymeric materials that may be used with oleamide include, but are not limited to, polyethylene based polymers, such as low density polyethylene (LDPE), linear low density polyethylene (LLDPE), and ethylene vinyl acetate (EVA), and polypropylene based polymers, such as homo-polypropylene and co-polypropylene, and a blend thereof.

In one embodiment, a valve stem 30 may be formed from a material comprising about 98.5 wt. % of HDPE/LLDPE/LDPE and about 1.5 wt. % of oleamide, which was formulated by compounding about 70 wt. % of HDPE, such as Marlex® 9708 HDPE from Chevron Phillips Chemical Company, and about 30 wt. % of Polybatch® CE505 from A. Schulman, which included about 95 wt. % of LLDPE/LDPE carrier and about 5 wt. % of oleamide. A valve including such a valve stem can provide a torque of about 0.5 in·lbs to about 2.0 in·lbs, which can be maintained after an extended time in storage and throughout the life of a valve. Further, field evaluations have indicated that such a torque range of about 0.5 in·lbs to about 2.0 in·lbs is an acceptable torque range for a valve for urostomy pouches.

Referring to FIGS. 5-8, the stem portion, below the grasping region 68 may include a barb element 88 on the tubular portion. The barb element 88 is adapted to permit connecting a discharge tube or other fluid conduit 90 onto the end 92 of the stem portion 30 and to temporarily secure the tube 90 to the stem portion 30.

The valve 22 may further include a cap or closure 94 that is configured to close off the stem end 92. The cap 94 can be formed from a material similar to the grasping region insert 74 (the TPE material) which is sufficiently soft and pliable to allow a user to readily and comfortably position the cap 94 on the stem end 92. The cap 94 can include an inner plug 95 that fits into stem end 92 or rests abutting the end 92 to provide a more secure seal of the valve 22. The cap 94 may also include a ring member 96 that fits over the tubular stem end 92 with a tether 98 to secure the cap 94 to the valve 22. The ring member 96 is configured to be positioned between the barb element 88 and the grasping region 68 to prevent interfering with attachment of the discharge tube 90 to the stem portion 30.

It will be appreciated that when the pouch 10 is worn during the day, the valve 22 will likely be closed, and the pouch 10 emptied when it is convenient to the user. When a user is bedridden or during the nighttime, for example when sleeping, the user will likely connect the discharge tube or conduit 90 to the valve 22, leaving the valve 22 open, so that fluids can drain directly to a collection container, such as, for example, a night drainage bag (not shown).

Figure 7:
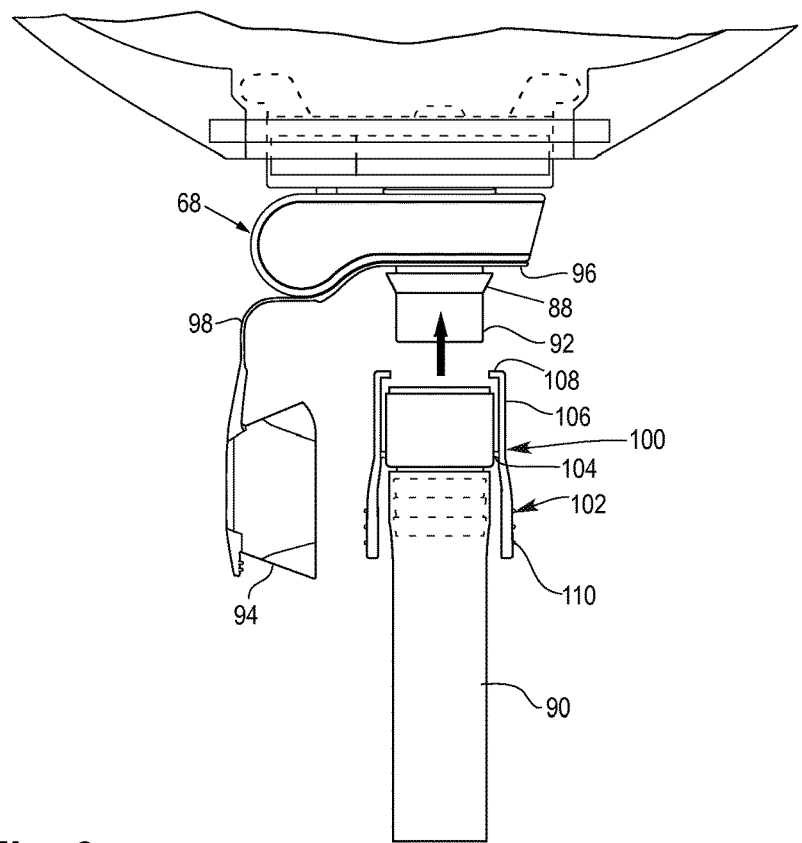
FIG. 7 is a view of the pouch and valve of FIG. 6 with a discharge tube being connected to a stem portion of the valve.
Figure 8:
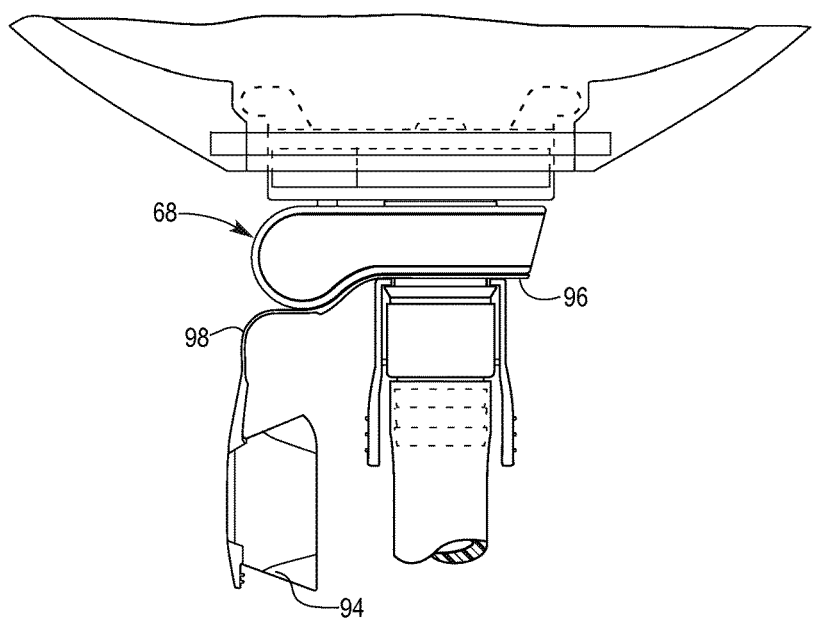
FIG. 8 is a view of the pouch and valve of FIGS. 6 and 7 with the discharge tube connected to the valve stem.
Figure 9:
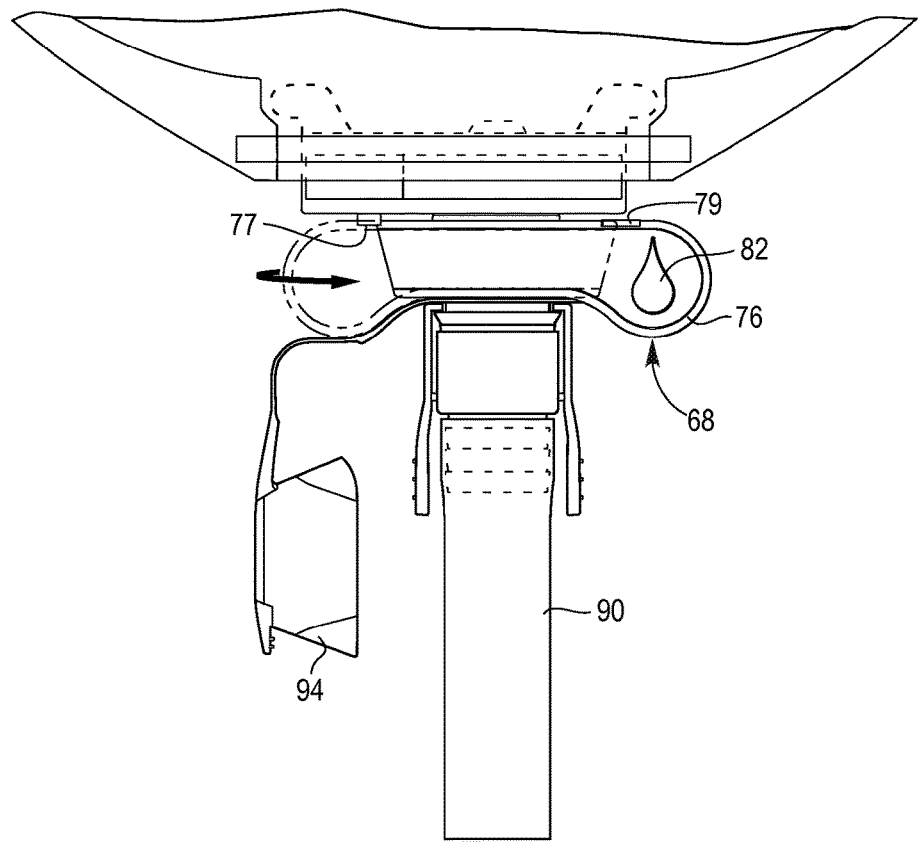
FIG. 9 is a view similar to FIG. 8 with the valve rotated to the open position.

To this end, as seen in FIGS. 7-9, the extension or discharge tube 90 can be attached to the valve stem end 92. The discharge tube 90 includes a connector portion 100 that fits over the stem end 92, and preferably secured to the barb element 88 below the grasping portion 68. It will be understood that the discharge connector portion 100 can be fitted on the stem end 92 when the cap 94 is removed.

The connector portion 100 includes flexible arms 102 that each has a living hinge 104. One end 106 of each arm 102 terminates in an inwardly oriented finger 108. An opposing end 110 of the arm 102 is configured for a user to pinch the arm 102 so as to pivot the arm 102 about the hinge 104. In a resting state, the arms 102 are biased inwardly, toward the tube 90. Thus, when pinching the arms 102 toward one another (inward, toward the tube 90), the fingers 108 are urged outwardly. The fingers 108 are positioned such that when the discharge tube 90 is connected to the stem end 92, the fingers 108 are located above the barb element 88 as illustrated in FIG. 8. This prevents undesired pull-out of the discharge tube 90 from the stem portion 30.

In a present discharge tube 90, the connector portion 100 is configured such that the connector portion 100 and discharge tube 90 can freely rotate about the stem end 92, without twisting the valve 22. That is, there is sufficient tolerance between the connector portion 100, in conjunction with the stem portion 30 material, to allow the discharge tube 90 to rotate. In this manner, there is less opportunity for the tube 90 or pouch 10 to become twisted or pinched if, for example, the user rolls over while resting, which could otherwise reduce or stop flow from the pouch 10. The connection is, however, liquid-tight, to prevent leakage.

Examples and Test Data

Valve samples were made using a polymer composition formulated with HDPE and a lubricating agent. The valve samples comprising different lubricating agents were compared with control valves, which were topically lubricated with silicone oil. Initial torque values of the valve samples (i.e. torque values for a first actuation of sample valves) and the control valves were measured and summarized in Table 1 below.

TABLE 1

Initial Torque for Valves

| Lubricant | Wt. %* | Sample Size | Ave. Peak Torque (in·lbs) | NOTES |
|---|---|---|---|---|
| CONTROL | n/a | 200 | 1.21 | Needle dosing of silicone oil (Dow Corning 200 ® 350 cSt) in about 0.05 to 0.10 g/part directly applied onto a valve stem. |
| Erucamide | 1 | 60 | 1.27 | |
| | 1.5 | 60 | 1.19 | |
| | 2 | 60 | 0.96 | |
| | 2.5 | 60 | 0.91 | Screw slippage |
| | 3 | 60 | 0.86 | Screw slippage |
| silicone compound-A | 3.5 | 15 | 3.16 | High torque |
| | 4 | 15 | 3.41 | High torque |
| | 5 | 15 | 2.94 | High torque |
| | 6 | 15 | 2.88 | High torque |
| | 7 | 15 | 2.94 | High torque; Parts showed sign of delamination. |
| | 8 | 15 | 2.75 | High torque; Parts showed sign of delamination. |
| | 9 | 15 | 2.78 | High torque; Parts showed sign of delamination. |
| | 12 | 15 | 2.64 | High torque; Parts showed sign of delamination. |
| | 15 | 15 | 2.51 | High torque; Parts showed sign of delamination. |
| silicone compound-B | 13 | 25 | 3.3 | High torque |
| | 17 | 25 | 2.96 | High torque |
| | 20 | 25 | 2.76 | High torque |
| silicone oil master batch | 3.5 | 50 | 3.06 | High torque |
| | 5 | 50 | 2.56 | High torque |
| | 7 | 50 | 1.40 | Parts showed sign of delamination. |
| teflon compound | 2 | 50 | 6.03 | High torque |
| oleamide | 1.5 | 100 | 1.26 | 0.2% oleamide in the valve body |
| | 1.5 | 786 | 1.09 | 0.2% oleamide in the valve body; Tested after about 1 month of storage time. |

*A lubricant in the listed weight % was added to a valve stem. No lubricant was added to a valve body unless otherwise noted in the table.

The valve samples and control valves were constructed similar to a valve 100 shown in FIGS. 12-13. The valve 100 is similarly configured to the valve of FIGS. 1-10 except a valve stem 102, as best shown in FIG. 13, has a split post 104.

Torque values were measured using a Shimpo digital torque meter (model# TNP-5). The torque meter was connected to a computer including Shimpo software and Excel for recording and analyzing torque data. For torque measurement, a valve was actuated using a lever on the top of the torque meter in a counter-clockwise direction. For a single actuation, the valve was rotated 360° in one continuous motion in about 3 seconds. For the purpose of this disclosure, the peak of the recorded torque values is used as the torque value for the valve. Thus, torque values in this disclosure are understood as a peak torque value of a valve, even if it is not expressly noted as a peak torque value. In Table 1 above, average peak torque values of valve samples are provided.

The control valves included a valve stem 102 and a valve body 106, which were made from HDPE. Neither the valve stem nor the valve body contained any lubricating agent. The control valves were subsequently lubricated by needle dosing the valve stem using Dow Corning 200® silicone oil having a viscosity of 350 cSt. In the dosing step, about 0.05 to about 0.10 g of the silicone oil was applied onto a corner 108 of the valve stem 102 (FIG. 13) using a needle applicator. The lubricated valve stem 102 was then assembled with the valve body 106 using a twist motion, during which the valve stem 102 was rotated about 270 degrees in the valve body 106, thereby wicking and spreading the silicone oil between the valve stem 102 and the valve body 106. 200 control valves were tested for a torque value for opening a valve for a first time from a closed position. An average peak torque of the 200 control valves was 1.21 in·lbs.

Although the topically lubricated control valves can have acceptable initial torque values, the torque can increase after an extended period of time in storage. This is because silicone oil has a tendency to flow away from where it is needed and leave dry spots, thereby increasing friction between the valve stem and the valve body in those dry spots. As shown in Table 2 below, an average initial torque for 200 control valves, which were tested about 1-2 weeks after topical application of silicone oil, was about 2.65 in·lbs. Such a high torque can make manipulation of the valve difficult for urostomy pouch users. However, during the first rotation of the valve, silicone oil is wicked and spread again. Thus, an average torque for a subsequent second opening of the valve drops to about 1.18 in·lbs.

TABLE 2

Torque for Valves with Topically Applied Silicone Oil

| | Control valve samples with topically applied silicone oil (sample size = 200) | |
|---|---|---|
| | First Actuation | Second Actuation |
| Average | 2.65 | 1.18 |
| Minimum | 1.09 | 0.71 |
| Maximum | 3.39 | 2.69 |
| Standard Deviation | 0.288 | 0.196 |

Thus, to solve this problem of the topically lubricated valves, valve samples including a lubricant incorporated into a valve stem matrix and/or a valve body matrix were prepared. Referring back to Table 1, valve samples including erucamide in differing quantities were prepared. These valve samples included a valve stem formed from a polymer compound comprising Marlex® 9708 HDPE and a specific quantity of erucamide. The valve body did not include any lubricant. 60 valve samples including a valve stem comprising 1 wt. % erucamide were prepared and tested. An average torque value for a first opening of these 60 valve samples was 1.27 in·lbs. 60 valve samples including a valve stem comprising 1.5 wt. % erucamide were prepared and tested. An average torque value for a first opening of these 60 valve samples was 1.19 in·lbs. 60 valve samples including a valve stem comprising 2 wt. % erucamide were prepared and tested. An average torque value for a first opening of these 60 valve samples was 0.96 in·lbs. 60 valve samples including a valve stem comprising 2.5 wt. % erucamide were prepared and tested. An average torque value for a first opening of these 60 valve samples was 0.91 in·lbs. However, the polymer compound including 2.5 wt. % erucamide was difficult to process in production as it caused screw slippage during the molding step. 60 valve samples including a valve stem comprising 3 wt. % erucamide were prepared and tested. An average torque value for a first opening of these 60 valve samples was 0.86 in·lbs. However, the polymer compound including 3 wt. % erucamide was difficult to process in production as it caused screw slippage during the molding step.

Valve samples including a silicone compound in differing quantities were prepared. These valve samples included a valve stem formed from a polymer compound comprising Marlex® 9708 HDPE and a specific quantity of a silicone compound, that for brevity, has been identified herein as "silicone compound A", which is a proprietary composition that was sourced from Chroma Corp, McHenry, Ill. A valve body did not include any lubricant. 15 valve samples including a valve stem comprising 3.5 wt. % silicone compound A were prepared and tested. An average torque value for a first opening of these 15 valve samples was 3.16 in·lbs, which is too high for a urostomy valve. 15 valve samples including a valve stem comprising 4 wt. % silicone compound A were prepared and tested. An average torque value for a first opening of these 15 valve samples was 3.41 in·lbs, which is too high for a urostomy valve. 15 valve samples including a valve stem comprising 5 wt. % silicone compound A were prepared and tested. An average torque value for a first opening of these 15 valve samples was 2.94 in·lbs, which is too high for a urostomy valve. 15 valve samples including a valve stem comprising 6 wt. % silicone compound A were prepared and tested. An average torque value for a first opening of these 15 valve samples was 2.88 in·lbs, which is too high for a urostomy valve. 15 valve samples including a valve stem comprising 7 wt. % silicone compound A were prepared and tested. An average torque value for a first opening of these 15 valve samples was 2.94 in·lbs, which is too high for a urostomy valve. Further, these samples showed signs of delamination, in which silicone compound was scratched off from the valve stem. 15 valve samples including a valve stem comprising 8 wt. % silicone compound A were prepared and tested. An average torque value for a first opening of these 15 valve samples was 2.75 in·lbs, which is too high for a urostomy valve. These samples also showed signs of delamination. 15 valve samples including a valve stem comprising 9 wt. % silicone compound A were prepared and tested. An average torque value for a first opening of these 15 valve samples was 2.78 in·lbs, which is too high for a urostomy valve. These samples also showed signs of delamination. 15 valve samples including a valve stem comprising 12 wt. % silicone compound A were prepared and tested. An average torque value for a first opening of these 15 valve samples was 2.64 in·lbs, which is too high for a urostomy valve. These samples also showed signs of delamination. 15 valve samples including a valve stem comprising 15 wt. % silicone compound A were prepared and tested. An average torque value for a first opening of these 15 valve samples was 2.51 in·lbs, which is too high for a urostomy valve. These samples also showed signs of delamination.

Valve samples including another silicone compound in differing quantities were prepared. These valve samples included a valve stem formed from a polymer compound comprising Marlex® 9708 HDPE and a specific quantity of a silicone compound, that for brevity, has been identified herein as "silicone compound B", which is a proprietary composition sourced from PolyOne, McHenry, Ill. The valve body did not include any lubricant. 25 valve samples including a valve stem comprising 13 wt. % silicone compound B were prepared and tested. An average torque value for a first opening of these 25 valve samples was 3.3 in·lbs, which is too high for a urostomy valve. 25 valve samples including a valve stem comprising 17 wt. % silicone compound B were prepared and tested. An average torque value for a first opening of these 25 valve samples was 2.96 in·lbs, which is too high for a urostomy valve. 25 valve samples including a valve stem comprising 20 wt. % silicone compound B were prepared and tested. An average torque value for a first opening of these 25 valve samples was 2.76 in·lbs, which is too high for a urostomy valve.

Valve samples made from a polymer compound including master batch polymer pellets containing silicone oil, with amounts of the master batch polymer pellets containing silicone oil in differing quantities were prepared and are referred to in Table 1 above as "silicone oil master batch." The silicone oil master batch is a proprietary composition sourced from A. Schulman. These valve samples included a valve stem formed from a polymer compound comprising Marlex® 9708 HDPE and a specific quantity of the master batch polymer pellets containing silicone oil. The valve body did not include any lubricant. 50 valve samples including a valve stem comprising 3.5 wt. % of the master batch polymer pellets containing silicone oil were prepared and tested. An average torque value for a first opening of these 50 valve samples was 3.06 in·lbs, which is too high for a urostomy valve. 50 valve samples including a valve stem comprising 5 wt. % of the master batch polymer pellets containing silicone oil were prepared and tested. An average torque value for a first opening of these 50 valve samples was 2.56 in·lbs, which is too high for a urostomy valve. 50 valve samples including a valve stem comprising 7 wt. % of the master batch polymer pellets containing silicone oil were prepared and tested. An average torque value for a first opening of these 50 valve samples was 1.40 in·lbs. However, these valve stems showed signs of delamination.

50 valve samples including a valve stem formed from a polymer compound comprising Marlex® 9708 HDPE and 2 wt. % Teflon® compound, which is a proprietary composition sourced from PolyOne, were prepared and tested. The valve body did not include any lubricant. An average torque value for a first opening of these 50 valve samples was 6.03 in·lbs, which is too high for a urostomy valve.

Valve samples including oleamide were prepared. These valve samples included a valve stem comprising 1.5 wt. % oleamide and a valve body comprising 0.2 wt. % oleamide. The valve stem was formed from a polymer compound comprising 70 wt. % Marlex® 9708 HDPE and 30 wt. %

Polybatch® CE505, which included about 95 wt. % of LLDPE/LDPE and about 5 wt. % of oleamide. 100 valve samples were prepared and tested. An average torque value for a first opening of these 100 valve samples was 1.26 in·lbs. Further, 786 additional valve samples were tested after about one month after they were made. An average torque value for a first opening of these 786 valve samples after one month was 1.09 in·lbs. That is, the torque for these valve samples did not increase after one month storage time. In fact, the torque value decreased.

As shown in Table 1 and further discussed above, the valve samples including erucamide and oleamide exhibited promising initial torque values. Thus, further tests were performed to analyze torque performance of the valves over an extended period of use. An average life of a urostomy pouch including a valve is about 5 days. That is, a user typically wears a urostomy pouch for about 5 days before changing to a new pouch. A typical usage of a valve during those 5 days is less than 60 actuations, more typically around 30 actuations. One actuation is defined as a 360 degree rotation of a valve from a closed position.

Figure 14:
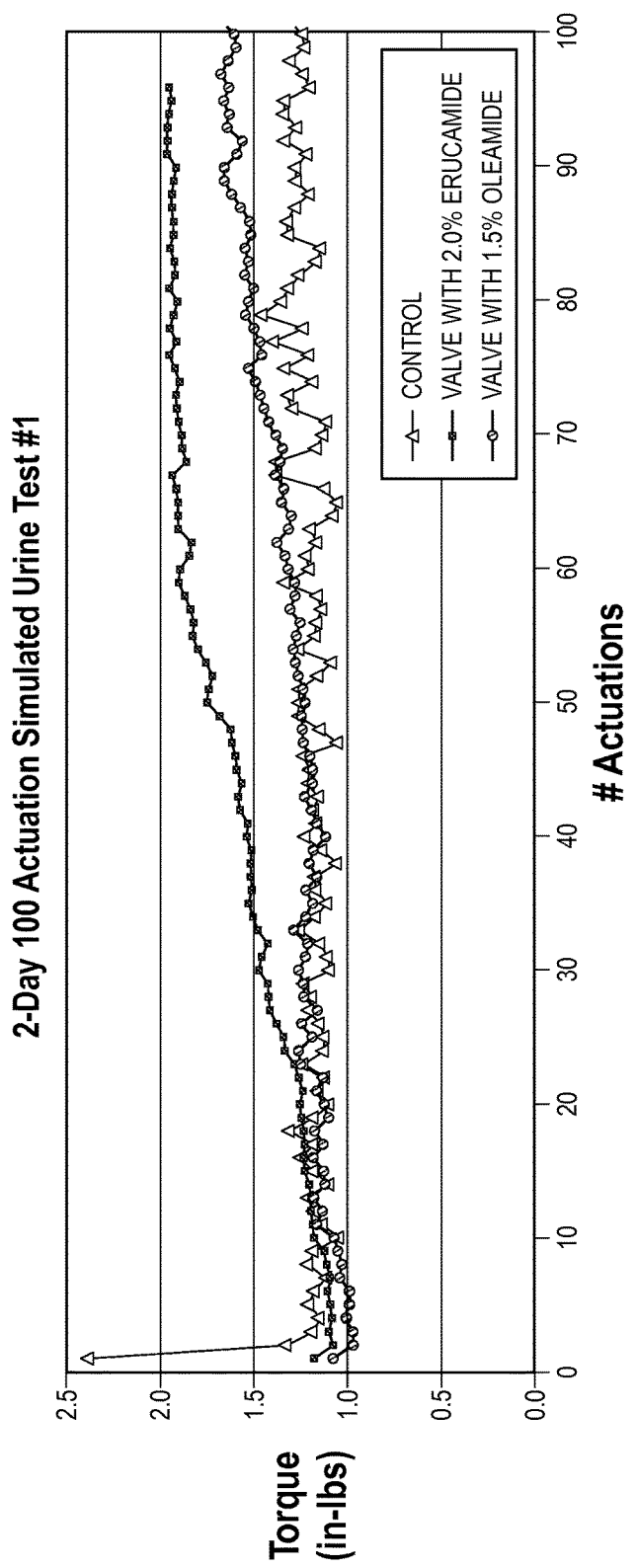
FIG. 14 is a graph depicting torque v. number of valve actuations for valve samples for 100 valve actuations over a 2-day period.

In Test#1, five control valves, five valve samples comprising 2.0 wt. % erucamide, and five valve samples comprising 1.5 wt. % oleamide were evaluated for 100 valve actuations over a 2-day period using a simulated urine fluid. FIG. 14 shows a graph depicting torque v. number of valve actuations. Each data point in the graph represents an average torque value for five measurements.

The five control valves were topically lubricated with needle dosing of silicone oil, and were prepared the same as the control valves explained above with regard to Table 1 and Table 2. Five valve samples comprising 2.0 wt. % erucamide included a valve stem formed from a polymer compound comprising Marlex® 9708 HDPE and a 2.0 wt. % erucamide. The valve body of these samples did not include any lubricant. Five valve samples comprising 1.5 wt. % oleamide included a valve stem formed from a polymer compound comprising 70 wt. % Marlex® 9708 HDPE and 30 wt. % Polybatch® CE505, which included about 95 wt. % of LLDPE/LDPE and about 5 wt. % of oleamide. The valve body of these samples did not include any lubricant. The simulated urine fluid used for this test was a solution including 19.4 g/l urea, 8.0 g/l sodium chloride, 1.1 g/l magnesium heptahydrate, 0.6 g/l calcium chloride, and 970.9 g/l deionized water.

As shown in FIG. 14, the topically lubricated control valves exhibited valve sticking, which is indicated by a high initial torque value of about 2.4 in·lbs. The valve samples comprising 1.5 wt. % oleamide had consistently low torque values that fell within a target torque range of about 0.5 in·lbs to about 2.0 in·lbs throughout 100 actuations over 2 days without any valve sticking phenomenon. The valve samples comprising 2.0 wt. % erucamide exhibited similarly good low torque in the beginning, but the torque increased incrementally with the number of actuations and approached 2.0 in·lbs after about 60 actuations.

Figure 15:
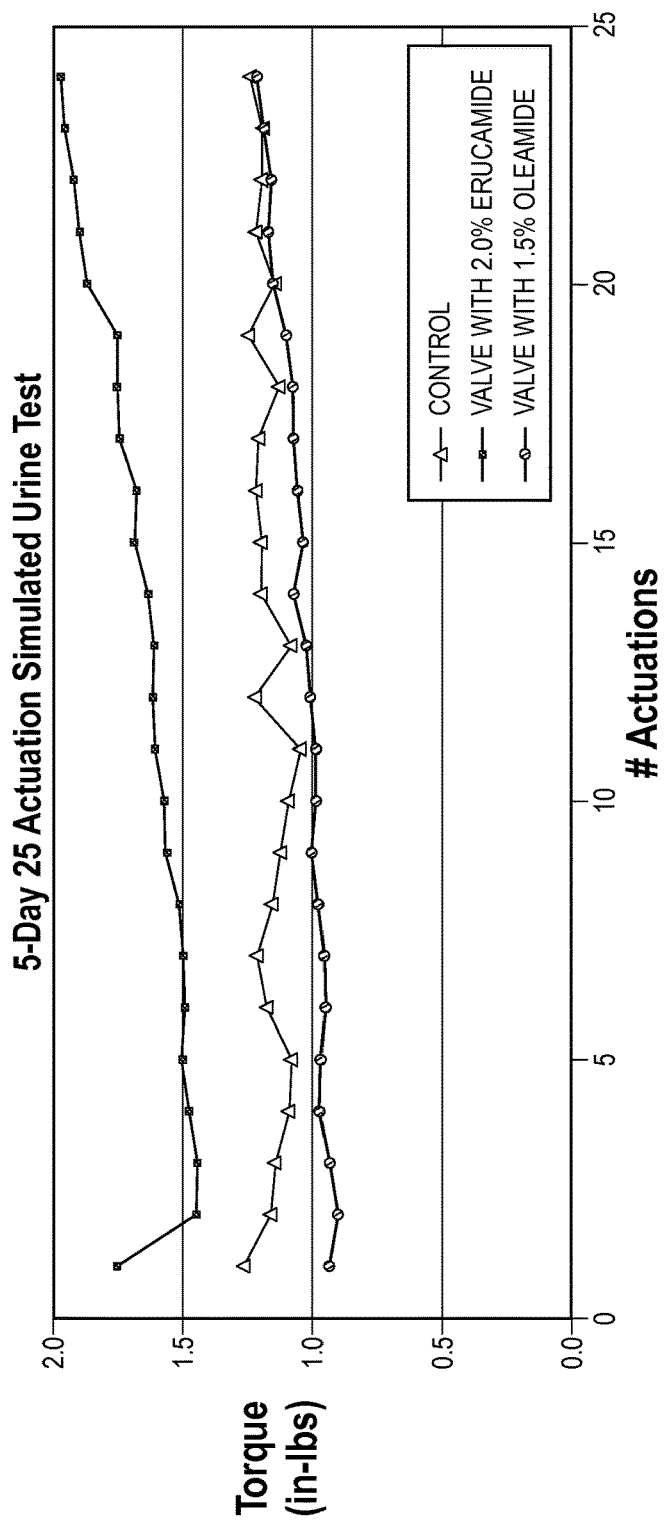
FIG. 15 is a graph depicting torque v. number of valve actuations for valve samples for 23 actuations over a 5-day period.

Test#1 was an exaggerated simulation of an actual valve usage. To more closely simulate the real life valve usage, Test#2 was performed for 23 actuations over a 5-day period. FIG. 15 depicting torque v. number of valve actuations for this test. For this test, the sample size was 15. That is, 15 samples for each of the control valve, 2.0 wt. % erucamide valve, and 1.5 wt. % oleamide valve were prepared and tested. Thus, each data point represents an average torque value of 15 torque measurements.

As shown in FIG. 15, the control valves and the valve samples including 1.5 wt. % had similarly low torque throughout 23 actuations over 5 days. Since the control valves were tested shortly after the topical silicone oil application, they did not show an initial spike in torque. However, the valve samples comprising 2.0 wt. % erucamide had a significantly higher torque when compared to the valve samples comprising 1.5 wt. % oleamide. Further, users who evaluated the sample valves indicated that they noticed stiffening of the valves over time with the valve samples comprising 2.0 wt. % erucamide. As such, these test results confirms the surprising effect of the oleamide in valves. Although, oleamide and erucamide are considered as similar slip agents in some industries, such as the packaging industry, in the present application of urostomy valves, depending on the geometry of the valve components, it is believed that adding oleamide in quantities greater than about 0.1 wt. % in a valve matrix can provide a valve having a substantially lower torque when compared to those including erucamide or other lubricating agents.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A valve that is sealable to an associated container having an interior, the valve adapted to permit and stop flow of fluid from the container interior, the valve comprising:
    a valve body sealable to the container, the valve body having a stem receiving region formed therein, the valve body including a fluid receiving region in communication with the container interior;
    a valve stem mounted to the valve body, the valve stem including a hollow tubular member defining a central bore, the valve stem positioned in the stem receiving region and adapted for rotation within the stem receiving region, the valve stem including a stem opening in a portion of a wall thereof, the valve stem being rotatable between an open position to align the stem opening with the valve body fluid receiving region to permit flow from the fluid receiving region through the valve, and a closed position to misalign the stem opening with the valve body fluid receiving region to stop flow through the valve,
    the valve stem having a grasping portion spaced from the valve body, the grasping portion adapted to rotate the valve stem within the stem receiving region to move the valve between the open and closed positions, and
    wherein at least a portion of the valve stem that is in contact with the stem receiving region is formed from a material essentially consisting of a rigid polymeric material selected from the group consisting of a polyethylene-based polymer, a polypropylene-based polymer, and blends thereof, and about 0.5 wt. % to about 5 wt. % oleamide.

2. The valve of claim 1, wherein at least the portion of the valve stem that is in contact with the stem receiving region is formed from a material essentially consisting of a polymeric blend comprising polyethylene and about 1.5 wt. % to about 2 wt. % oleamide.

3. The valve of claim 1, wherein the valve stem is formed from a material essentially consisting of about 98 wt. % to about 98.5 wt. % of a polymeric blend including HDPE, LLDPE, and LDPE, and about 1.5 wt. % to about 2 wt. % oleamide.

4. The valve of claim 1, wherein the grasping portion includes a frame, wherein the hollow tubular member and the frame are formed as a unitary member, wherein the unitary member is formed from a material comprising about 98 wt. % to about 98.5 wt. % of a polymeric blend including HDPE, LLDPE, and LDPE, and about 1.5 wt. % to about 2 wt. % oleamide.

5. The valve of claim 1, wherein the valve has an average torque value between about 0.5 in·lbs to about 2.0 in·lbs after 1 month in storage and throughout 5 days of use.

6. The valve of claim 1, wherein the valve body is formed from a material comprising 0.01 wt. % to about 0.5 wt. % oleamide.

7. A valve that is sealable to an associated container having an interior, the valve adapted to permit and stop flow of fluid from the container interior, the valve comprising:
a valve body sealable to the container, the valve body having a stem receiving region formed therein, the valve body including a fluid receiving region in communication with the container interior;
a valve stem mounted to the valve body, the valve stem including a hollow tubular member defining a central bore, the valve stem positioned in the stem receiving region and adapted for rotation within the stem receiving region, the valve stem including a stem opening in a portion of a wall thereof, the valve stem being rotatable between an open position to align the stem opening with the valve body fluid receiving region to permit flow from the fluid receiving region through the valve, and a closed position to misalign the stem opening with the valve body fluid receiving region to stop flow through the valve,
the valve stem having a grasping portion spaced from the valve body, the grasping portion adapted to rotate the valve stem within the stem receiving region to move the valve between the open and closed positions, and
wherein at least a portion of the valve stem that is in contact with the stem receiving region is formed from a material essentially consisting of about 98 wt. % to about 98.5 wt. % of a polymeric blend including HDPE, LLDPE, and LDPE, and about 1.5 wt. % to about 2 wt. % oleamide.

* * * * *